(12) United States Patent
Geerke

(10) Patent No.: US 7,011,850 B2
(45) Date of Patent: Mar. 14, 2006

(54) DOSAGE FORMS HAVING A BARRIER LAYER TO LASER ABLATION

(75) Inventor: Johan H. Geerke, Los Altos, CA (US)

(73) Assignee: Alza Corporation, Mountain View, CA (US)

( * ) Notice: Subject to any disclaimer, the term of this patent is extended or adjusted under 35 U.S.C. 154(b) by 401 days.

(21) Appl. No.: 09/735,989

(22) Filed: Dec. 13, 2000

(65) Prior Publication Data

US 2002/0071866 A1 Jun. 13, 2002

Related U.S. Application Data

(60) Provisional application No. 60/172,371, filed on Dec. 16, 1999.

(51) Int. Cl.
*A61K 9/22* (2006.01)
*A61K 9/24* (2006.01)

(52) U.S. Cl. ...................................... 424/473; 424/468
(58) Field of Classification Search ................. 424/457, 424/468, 473, 472, 464, 463, 469, 408; 604/892.13
See application file for complete search history.

(56) References Cited

U.S. PATENT DOCUMENTS

| | | | |
|---|---|---|---|
| 2,799,241 | A | 7/1957 | Wurster |
| 3,854,770 | A | 12/1974 | Grise et al. |
| 3,916,899 | A | 11/1975 | Theeuwes et al. |
| 4,063,064 | A | 12/1977 | Saunders et al. |
| 4,088,864 | A | * 5/1978 | Theeuwes ................... 219/121 |
| 4,285,987 | A | 8/1981 | Ayer et al. |
| 4,519,801 | A | 5/1985 | Edgren |
| 4,612,008 | A | 9/1986 | Wong et al. |
| 4,783,337 | A | 11/1988 | Wong et al. |
| 4,892,778 | A | 1/1990 | Theeuwes et al. |
| 4,915,954 | A | 4/1990 | Ayer et al. |
| 5,049,722 | A | 9/1991 | Corfe et al. |
| 5,082,668 | A | 1/1992 | Wong et al. |
| 5,140,127 | A | 8/1992 | Stroud et al. |
| 5,630,808 | A | * 5/1997 | Magruder et al. ........ 604/892.1 |
| 5,767,482 | A | 6/1998 | Turner |
| 5,783,793 | A | 7/1998 | Emerton et al. |

FOREIGN PATENT DOCUMENTS

| | | |
|---|---|---|
| GB | 2174299 | 11/1986 |
| HU | P0104993 | 5/2002 |
| HU | P0201626 | 12/2002 |

OTHER PUBLICATIONS

Y. W. Francis Lam, "Stereoselectivity: An Issue of Significant Importance in Clinical Pharmacology," Pharmacotherapy, vol. 8 ( No. 3), p. 147–157, ( Jan. 4, 1988).

Kenneth Williams and Edmund Lee, "Importance of Drug Enantiomers in Clinical Pharmacology," Drugs, ADIS Press Limited (U.S.), p. 333–354, ( Jan. 4, 1985).

* cited by examiner

Primary Examiner—James M. Spear
(74) Attorney, Agent, or Firm—Angela N. Nwaneri

(57) ABSTRACT

A dosage form for delivery of a therapeutic agent to a subject is described. The dosage form contains: (a) an outer wall defining an interior compartment; (b) within the interior compartment, a therapeutic agent; (c) at least one exit orifice formed by laser ablation of the outer wall for release of the agent therethrough, and (d) a barrier layer disposed between the outer wall and the interior compartment in at least a region corresponding to the exit orifice. The barrier layer comprises a material that allows the barrier layer to remain intact during laser-formation of the at least one exit orifice in the outer wall. Also disclosed is a method for controlling the depth of laser ablation of a dosage form during laser formation of an exit orifice in an outer wall of the dosage form.

12 Claims, 2 Drawing Sheets

DOSAGE FORMS HAVING A BARRIER LAYER TO LASER ABLATION

This application claims the benefit of Provisional Application No. 60/172,371, filed Dec. 16, 1999.

FIELD OF THE INVENTION

The present invention relates to dosage forms having an outer wall containing at least one laser-formed exit orifice. More particularly, the invention relates to dosage forms that include a barrier layer containing a material that allows the barrier layer to remain intact during laser-formation of the orifice(s). The invention also relates to methods for controlling the depth of laser ablation during formation of an orifice.

BACKGROUND OF THE INVENTION

A variety of Pharmaceutical dosage forms are known having one or more openings formed through an outer layer or layers on the surface of the dosage form. The openings generally allow release of contents from within an internal compartment of the dosage form to an external environment of use. Many different types of dosage forms that utilize such openings include, for example, osmotic controlled delivery systems as described in U.S. Pat. Nos. 3,854,770 and 3,916,899. In general, such osmotic systems utilize osmotic pressure to generate a driving force for imbibing fluid into an internal compartment formed, at least in part, by a semipermeable wall that permits free diffusion of fluid but not drug or osmotic agent(s). Typically, at least one exit orifice is formed through the semipermeable membrane. Following administration of the dosage form to a suitable fluid environment, such as the gastrointestinal tract or other body cavity or body tissue, fluid imbibition results in a deliverable drug formulation being released from within the compartment through the at least one exit orifice at a controlled rate.

Osmotic systems can be manufactured, for example, by forming an internal compartment containing an active agent and other ingredients, such as an osmagent and osmopolymer, into a solid or semisolid by ballmilling, calendaring, stirring or rodmilling and then pressing the internal compartment into a desired shape. In one embodiment, the internal compartment contains a drug layer and an osmotic material layer. Alternatively, a liquid therapeutic agent may be rendered into a solid or semi-solid shape, by for example, enclosing the liquid agent in a water-soluble capsule coated with an osmotic material layer. Finally, to prepare an osmotic delivery system, a semipermeable outer wall is applied to the solid or semisolid shape and at least one exit orifice is laser-formed through the semipermeable wall. The semipermeable wall is typically formed by dissolving the semipermeable wall material in an appropriate solvent, such as acetone or methylene chloride, and applying to the pressed shape by a suitable technique (U.S. Pat. Nos. 4,892,778; 4,285,987; 2,799,241).

After application of the semipermeable wall, the wall is dried and at least one exit orifice is formed in the device. Depending on the properties of the active agent and other ingredients within the internal compartment, and on the desired release rate of the active agent from the dosage form, at least one orifice is formed. The orifice(s) may range from a single large orifice containing an entire surface of the dosage form to one or more smaller orifices. Processes and apparatus for forming orifices in dosage forms using a laser beam have been described in the art, see for example, U.S. Pat. Nos. 4,063,064 and 5,783,793.

A problem encountered with the formation of exit orifices by laser drilling is the imprecise control of the depth of penetration by the laser beam. On the one hand, the laser beam must penetrate the outer wall to a depth sufficient to provide an exit orifice for operation of the device. On the other hand, it is undesirable for the laser beam to penetrate to a significant extent beyond the outer wall. For solid dosage forms, i.e., dosage forms having a compressed tablet core surrounded by a semipermeable membrane, penetration of the laser beam beyond the depth of the semipermeable wall may result in loss of some core material from the internal compartment. Although this loss can generally be minimized and controlled within a tolerance range, it would be highly advantageous to eliminate material loss. For liquid dosage forms, i.e., a liquid-filled capsule surrounded by an osmotic layer and coated with a semipermeable wall, penetration of the laser beam beyond the depth of the overlying layer(s) may result in piercing of the capsule wall resulting in unacceptable leakage of the liquid contents from the dosage form. Therefore, there exists a need in the art to eliminate material loss from a dosage form.

BRIEF SUMMARY OF THE INVENTION

Accordingly, it is an object of the invention to provide a dosage form that includes a layer that provides for easy control of the depth of penetration of a laser beam during formation of at least one exit orifice in a dosage form.

It is another object of the invention to provide a dosage form that includes a layer that remains intact during and after formation of an exit orifice, such that the contents of the internal compartment are retained until administration of the dosage form.

It is another object of the invention to provide methods for controlling the depth of penetration of a laser beam during formation of an exit orifice in a dosage form.

In one aspect, the invention includes a dosage form for delivery of a therapeutic agent to a subject. The dosage form contains: (a) an outer wall defining an interior compartment; (b) within the interior compartment, a therapeutic agent; (c) an exit orifice formed by laser ablation of said outer wall; and (d) a barrier layer disposed between the outer wall and the interior compartment in at least a region proximate to the exit orifice. The barrier layer contains a material that is substantially impervious to laser ablation from a selected laser and selected laser operating conditions that result in laser ablation of the outer wall material to form an exit orifice. Accordingly, the barrier layer contains a material that does not absorb the laser energy. Rather, the barrier layer contains a material that either reflects the laser energy or that transmits the laser energy, i.e., is transparent to the laser energy. Suitable materials may be selected for various laser types and exemplary materials are described below.

In addition, the barrier layer contains a material that permits release of the therapeutic agent through the at least one exit orifice following administration of the dosage form to an environment of use. For example, the barrier layer may contain material that is dissolvable within the fluid environment of use or may contain a structure and/or composition that otherwise permits passage of therapeutic agent therethrough, for example a thin film that readily tears or ruptures following administration of the dosage form to an environment of use, or a non-contiguous film having microscale or smaller sized pores for permitting passage of therapeutic agent therethrough.

In one embodiment, the barrier layer encases or surrounds the interior compartment. In another embodiment, the barrier layer is disposed only in a region corresponding to the area or the at least one exit orifice. The interior compartment of the dosage form may contain a solid or semisolid composition including the therapeutic agent and other optional ingredients. Such optional ingredients include, for example, an osmagent and/or osmopolymer. In a preferred embodiment, the internal compartment contains a compressed tablet containing a drug layer and an osmotic material layer. The barrier layer is disposed between the outer wall and the underlying solid or semisolid core of the dosage form.

In another embodiment, the interior compartment of the dosage form may contain a liquid-state therapeutic agent contained within a water-soluble capsule. The liquid-state therapeutic agent contained in the capsule is surrounded by, or otherwise in contact with, an osmotically-active material layer, which underlies the semipermeable outer wall. For embodiments wherein dosage form includes a liquid-state therapeutic agent, the barrier layer may be disposed between the outer wall and the underlying water-soluble capsule on either side of the osmotic material layer. Alternatively, the water-soluble capsule may be fabricated to function as the barrier layer by including a material that is substantially impervious to laser ablation within the capsule material.

In another embodiment, the invention includes an improvement in an osmotic dosage form of the type having an outer semipermeable wall defining an interior compartment containing a therapeutic agent and an osmotic agent, and including at least one laser-formed passageway in the semipermeable wall for release of the therapeutic agent. The improvement in the dosage form includes a barrier layer disposed between the interior compartment and the semipermeable wall in at least a region corresponding to the passageway. The barrier layer functions to prevent the laser beam from piercing into the interior compartment of the dosage form during laser-formation of the passageway in the semipermeable wall.

The invention further provides methods for controlling the penetration depth of a laser beam during formation of an exit orifice in a dosage form by laser ablation of an outer wall defining an interior compartment containing a therapeutic agent. The method contains including in the dosage form, a barrier layer disposed between the outer wall and the interior compartment in at least a region corresponding to where the exit orifice is to be formed. The barrier layer remains intact, i.e., is not ablated, during formation of the exit orifice in the outer wall of the dosage form. The barrier layer remains intact by virtue of a material incorporated into the barrier layer that either reflects the laser energy or that transmits the laser energy (thereby rendering the barrier layer transparent to the laser energy). In either embodiment, the laser energy is essentially not absorbed by the barrier layer such that little or no ablation of the barrier layer occurs during formation of the at least one exit orifice.

The invention further relates to methods for controlling the penetration depth of a laser during formation of an orifice in a dosage form via laser ablation of an outer wall surrounding a capsule defining an interior compartment containing a therapeutic agent. The method includes selecting a laser source and laser operating parameters capable of ablating the outer wall while simultaneously incapable of ablating the capsule.

In one embodiment of this aspect, the method further includes selecting a material for formation of the outer wall based on the selection of laser source and operating parameters such that the selected outer wall material is one that can be ablated by the selected laser source at the operating conditions.

Similarly, the material selected for formation of the capsule can be a material that is not ablated by the selected laser source and the selected operating conditions. More specifically, the selected capsule material can be one that reflects the laser energy or that is transparent to the laser energy. In yet another aspect of the invention, a method is provided for controlling depth of an orifice formed in a dosage form by a selected laser source at selected operating conditions, wherein the dosage form has an outer polymer wall surrounding an inner wall defining an interior compartment containing a therapeutic agent. The method includes selecting a material for formation of the outer wall that is ablated by the selected laser source and the operating conditions; and selecting a material for formation of the inner wall, a material that is not ablated by the selected laser source and selected operating conditions.

These and other objects and features of the invention will be more fully appreciated in view of the following detailed description of the invention and the accompanying drawings.

DETAILED DESCRIPTION OF THE INVENTION

The above-identified drawings are examples of various osmotic delivery system embodiments of the invention. As examples of the present invention, they should be viewed as merely exemplary of invention not limitations of the invention.

Figure 1A:
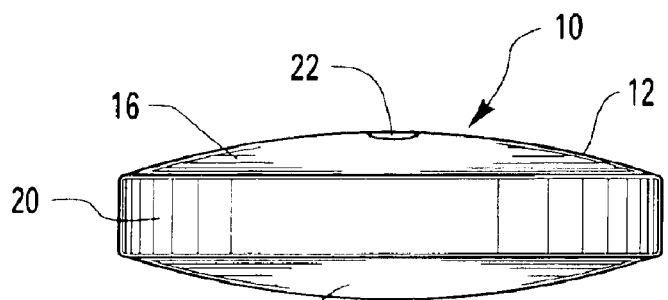
FIGS. 1A–1B are enlarged perspective and cut-away views of a solid osmotic dosage form according to the invention.
Figure 1B:
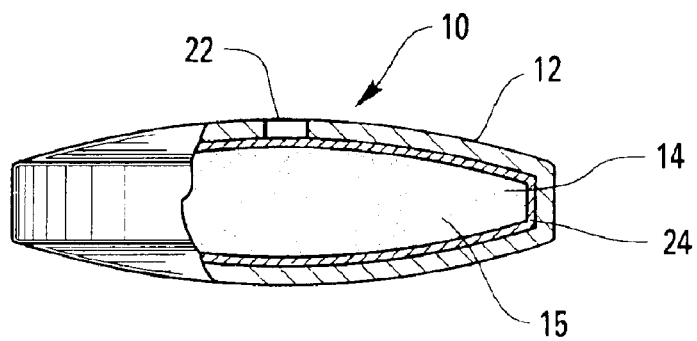

One example is shown in FIGS. 1A–1B. Dosage form 10 contains an outer wall 12 that defines an interior compartment 14, visible in the cut-away of FIG. 1B. As will be described below, outer wall 1 is composed of a material that is permeable to the passage of fluid, but is substantially impermeable to the passage of drug or therapeutic agent, e.g., a semipermeable material. Materials suitable for formation of the outer wall include synthetic and naturally occurring semipermeable polymer materials. In one embodiment, the polymer is a thermoplastic polymer. When a thermoplastic polymer is selected as the material for outer wall 12, outer wall 12 is essentially non-toxic and maintains its physical and chemical integrity during the delivery life of therapeutic agent from the device.

Internal compartment 14 of dosage form 10 includes a therapeutic agent 15 intended to be released from the dosage form 10 into the environment of use. The therapeutic agent can be either soluble, insoluble, or combinations thereof in the external fluid imbibed into the dosage form 10. Optionally included in the internal compartment 14 is an osmotic attractant or solute. A solute may be included when the therapeutic agent to be released from the device has limited solubility i.e., in the imbibed external fluid, such as tissue fluid, gastric juices, tear fluid, etc. The osmotic solute and/or the therapeutic agent is soluble in the fluid imbibed into internal compartment 14.

Exemplary osmotic attractants or solutes include, for example, magnesium sulfate, magnesium chloride, sodium chloride, lithium chloride, potassium sulfate, sodium carbonate, sodium sulfite, lithium sulfate, calcium bicarbonate, sodium sulfate, calcium sulfate, potassium acid phosphate, calcium lactate, magnesium succinate, tartaric acid, soluble carbohydrates such as raffinose, glucose, mixtures thereof, and the like. Solutes can be present initially in excess in any suitable physical form such as particles, crystals, pellets, tablets, strips, film, granules, etc.

As noted above, the therapeutic agent, and optionally the osmotic attractant or solute, are pressed into a solid or semi-solid shape using, for example, conventional tablet press techniques. In FIGS. 1A–1B dosage form 10 is depicted as having a conventional tablet shape for oral administration. The dosage form 10 tablet has a substantial surface 16, and a second substantial surface 18, and an edge 20. It will be appreciated, however, that a variety of dosage form shapes, including cylindrical, triangular, square, etc. may be employed in the invention. In addition, the solid dosage form may be formed in a capsule-shaped configuration.

An exit orifice 22, is formed by laser ablation on surface 16 of dosage form 10. Exit orifice 22, as shown in FIG. 1B, penetrates the thickness of outer wall 12. After administration of dosage form 10, the therapeutic agent in the internal compartment is released to the environment of use via the exit orifice 22. Disposed between the outer wall 12 and internal compartment 14, is a barrier layer 24. Barrier layer 24, as shown in FIG. 1B encases or surrounds the internal compartment 14.

As discussed below regarding FIG. 3, the barrier layer 24 is disposed between the outer wall 12 and internal compartment 14, just in a region corresponding to the exit orifice 22. In either of these embodiments, the barrier layer 24 can form a contiguous, non-porous film or a non-contiguous, porous film. When barrier layer 24 is a contiguous, non-porous film, the barrier layer 24 is deposited to a thickness sufficient to form an isotropic film. When barrier layer 24 is a non-contiguous porous film, barrier layer 24 is deposited on the pressed shape to form a film that may have smaller pores or micron-sized pores.

Barrier layer 24 is deposited on the pressed shape of a selected therapeutic agent prior to deposition of the semi-permeable wall to form barrier layer 24. The barrier layer 24 can be formed directly on the pressed shape, (FIG. 1B), or there can be layers of other materials deposited between the selected therapeutic agent and the barrier layer 24. Similarly, there can be intervening layers between the barrier layer 24 and the outer wall 12. The barrier layer 24 can be deposited, for example, by molding, air spraying, dipping or brushing a solvent-based solution of the barrier material onto the pressed shape or by other methods known in the art. The layer can be applied using an air suspension procedure, wherein the pressed shape is suspended and tumbled in a current of air and barrier layer forming material, or by a pan coating technique.

The barrier layer 24 contains material that is substantially impervious to laser ablation under selected laser equipment and laser operating conditions that result in laser ablation of the outer wall 12 material to form the exit orifice 22. Accordingly, the barrier layer 24 contains material that does not substantially absorb the laser energy. Rather, the barrier layer 24 contains material that either reflects the laser energy or that transmits the laser energy, i.e., is transparent to the laser energy.

In addition, the barrier layer 24 contains a material that permits release of a therapeutic agent through the exit orifice 22 following administration of the dosage form to an environment of use. For example, the barrier layer 14 may contain material that is dissolvable within the fluid environment of use, or may contain a structure and/or composition that otherwise permits passage of a therapeutic agent therethrough, i.e., a thin film that readily tears or ruptures following administration of the dosage form to an environment of use, or a non-contiguous film having microscale or smaller sized pores for permitting passage of the therapeutic agent therethrough.

In one preferred embodiment barrier layer 24 is formed using a laser energy reflecting material that is deposited between the outer wall 12 and the internal compartment 14 of the dosage form 10. For example, when a carbon dioxide laser is used, materials including carbon black, powdered stainless steel, powdered nickel, powdered iron, hydrous magnesium silicate (talc), powdered glass (Aerosil®), titanium dioxide, magnesium aluminum silicate, aluminum silicate (Bentonite), aluminum oxide and metallic chips or flakes, will reflect the laser energy.

The barrier layer 24 can also be formed using a laser energy transmitting material. For example, the laser energy transmitting material is effective to render the barrier layer 24 transparent to the laser beam, minimizing and/or preventing ablation of the barrier layer 24 during laser-formation of the passageway in the outer wall 12.

Typically, the selected laser energy reflecting or transmitting material is combined with a second material suitable for forming a thin film or layer about the preformed, solid or semi-solid dosage form. A variety of polymers are useful as the second material, including water soluble and non-water soluble polymers, and those described below for use in forming the outer wall 12 of the dosage form 10 are exemplary candidates. The polymers useful in the second material polymer can be either semi-permeable or permeable. The laser energy reflecting or transmitting material is mixed with the polymer material in a proportion that: (i) allows for formation of a layer or film on the preformed, shaped dosage form; and (ii) is effective to reflect or transmit the laser during formation of the exit orifice such that the barrier layer 24 is minimally, if at all, ablated.

The proportions of the polymer and the laser energy reflecting or transmitting material will vary depending on the nature of the polymer and the selected material, but typically, between about 5 to about 80 weight percent (wt %) of laser energy reflecting or transmitting material is incorporated into a polymer melt or solution. Preferably, between about 5 to about 50 wt % of laser energy reflecting or transmitting material, and more preferably between about 10 to about 30 wt % laser energy reflecting or transmitting material, is mixed with the polymer solution or melt.

After application of the barrier layer 24, the outer wall 12 is formed about the barrier-layer coated pressed shape. A semi-permeable outer wall 12 is formed by dissolving the wall material in an appropriate solvent, such as acetone or methylene chloride, and applying the solution to the pressed shape using, for example, one of the methods described above for application of the barrier layer.

After formation of the semi-permeable outer wall 12, the dosage form is dried and then the exit orifice 22 is formed via laser drilling. The barrier layer 24 defines the depth to which material is ablated and removed from the dosage form 10 by the laser energy. As shown in FIG. 1B, the laser energy effectively ablates the outer wall 12 material to form an exit orifice 22 therein, but minimally, if at all, ablates the barrier layer 24. The barrier layer 24 remains intact during laser formation of the exit orifice 22 by virtue of the laser energy either being reflected away from the barrier layer or passing through the barrier layer 24 without ablating the barrier layer 24.

Upon administration of the dosage form to a subject, such as a mammal, fluid from the external environment passes across the outer wall 12. Disposed between the outer wall 12 and the selected therapeutic agent, which can be a liquid, solid, slurry, semi-emulsified or a mixture thereof, and at least in the region corresponding to the exit orifice 22 is the barrier layer 24. In one embodiment, the second material employed in forming the barrier layer 24, i.e., the material in addition to the laser-reflecting material or the laser-transmitting material, is a water-soluble polymer. In this embodiment, the barrier layer 24 upon contact with the imbibed aqueous fluid swells, dissolves and/or becomes solubilized in the fluid, eventually weakening sufficiently for fluid to penetrate into the internal compartment 14 of the dosage form 10. As fluid is imbibed into the internal compartment 14, i.e., osmotically, hydrostatic pressure in the dosage form increases. Remaining barrier layer 24 in the region corresponding to the exit orifice 22, will typically tear or rupture allowing the therapeutic agent to be released from the dosage form 10 through the exit orifice 22.

It will be appreciated that barrier layer 24, when composed of a water-soluble polymer, can be deposited as a contiguous, non-porous film, as the film over a time period will solubilize and weaken in the presence of the imbibed fluid. The film, however, can also be deposited as a porous film, using techniques known in the art. The micropores in the film allow passage of the imbibed fluid. A porous film is particularly suitable for formation of a barrier layer 24 using a non-water soluble polymer as the second material.

Figure 2:
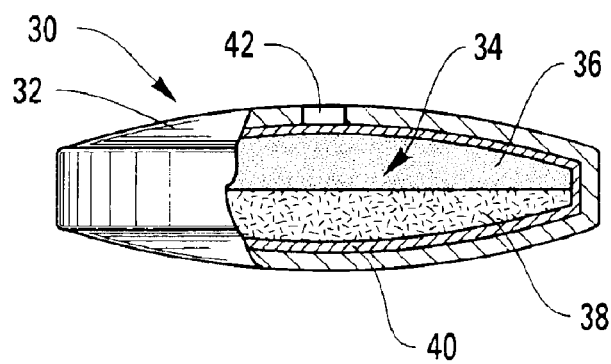
FIG. 2 is an enlarged, cut-away view of another embodiment of a solid osmotic dosage according to the invention.

Turning now to FIG. 2, a cut-away view of an osmotic dosage form is shown wherein the dosage form has a bilayer core. Dosage form 30 contains a semipermeable outer wall 32 that defines an internal compartment 34. Contained within the internal compartment 34 is a therapeutic agent layer 36 positioned adjacent the internal compartment 34 which is an expandable osmopolymer layer 38. The layers cooperate with each other to provide sustained controlled release of a therapeutic agent from the dosage form 30 during use through at least one suitably sized exit orifice 42 laser-formed through the semipermeable outer wall 32. Following administration of the dosage form 30 to a suitable fluid environment, such as the gastrointestinal tract or other body cavity or body tissue, fluid imbibition results in a deliverable drug-containing formulation being released from within the compartment through the at least one exit orifice 42 at a controlled and sustained rate. The therapeutic agent layer 36 includes a pre-selected therapeutic agent and, optionally, an osmotic solute, such as those recited above, admixed with the therapeutic agent along with other pharmaceutically acceptable excipients such as binders, lubricants, disintegrants, suspension agents, surfactants, diluents, stabilizers, antioxidants, colorants, plasticizers, and the like.

Suitable materials and methods for forming the expandable osmopolymer layer 38 of dosage form 30 are described, for example, in U.S. Pat. Nos. 4,519,801; 4,612,008; 4,783,337; 4,892,778 and 5,082,668.

Dosage form 30 of FIG. 2 typically includes a barrier layer 40 disposed between the outer wall 32 and the internal compartment 34. The barrier layer 40, as described above, includes a material that prevents the layer from being ablated during laser formation of an exit orifice 42 in the outer wall 32 of the dosage form 30.

Figure 3:
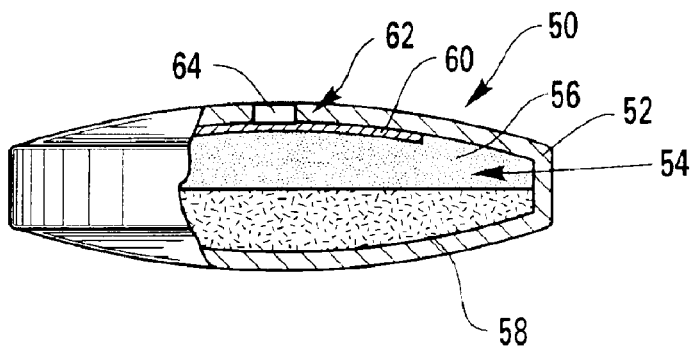
FIG. 3 is an enlarged view of another embodiment of a solid osmotic dosage form in accordance with the invention, wherein the barrier layer is positioned in a region corresponding to the exit orifice.

In another embodiment FIG. 3 shows a cut-away view of dosage form 50 showing that the dosage form 50 contains a permeable outer wall 52 and an internal compartment 54 housing a bilayer arrangement of an active agent layer 56 positioned adjacent an expandable osmopolymer layer 58. In this embodiment of the invention, a barrier layer 60 is disposed between the outer wall 32 and the internal compartment 34 in a region 62 corresponding to an exit orifice 64. In contrast to the previously described embodiment, i.e., FIG. 2, the barrier layer 40 does not completely surround or encase the internal compartment, but is disposed only in the region corresponding to the exit orifice 64.

Figure 4A:
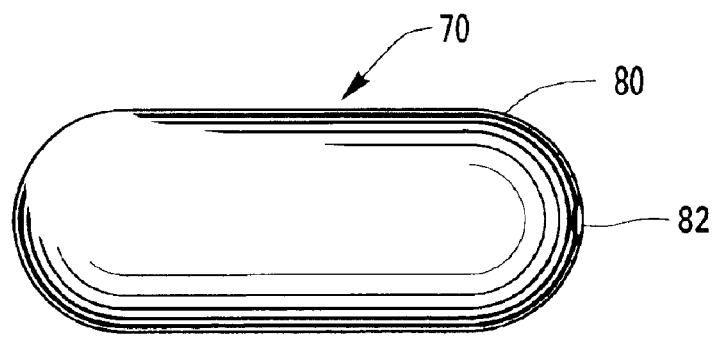
FIGS. 4A–4C are enlarged perspective and cut-away views of a liquid dosage form according to the invention.
Figure 4B:
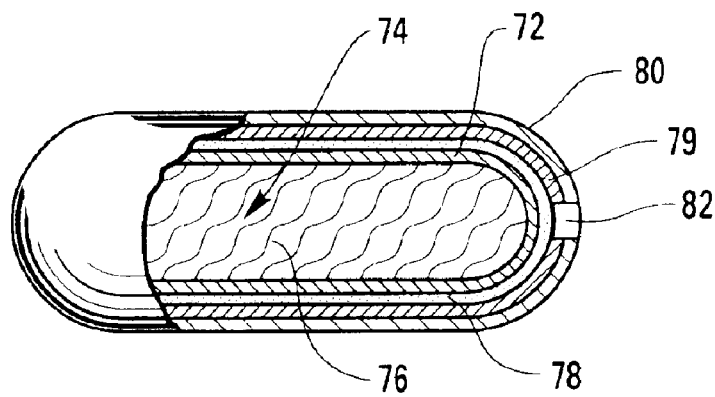
Figure 4C:
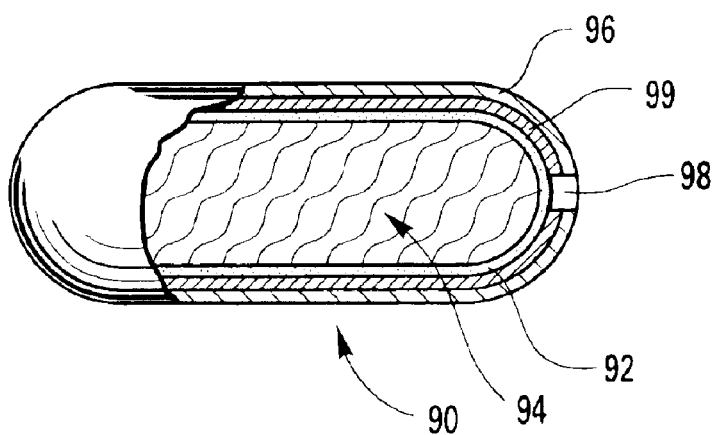

FIGS. 4A–4C illustrate another embodiment of the invention wherein the dosage form includes a therapeutic agent that is a liquid. With initial reference to the embodiments of FIGS. 4A–4B, an elongated or capsule-shaped osmotic dosage form 70 is shown in perspective view (FIG. 4A), and in a cut-away view (FIG. 4B). The dosage form 40 contains an inner capsule 72 that defines a reservoir 74 containing a liquid therapeutic agent 76. The inner capsule 72 is preferably composed of a water-soluble natural or synthetic polymer. Suitable materials are known to those of skill in the art.

The dosage form 70 further contains a barrier layer 78. Barrier layer 78 can either surround the inner capsule 72, as shown, or may surround only a portion of the inner capsule 72 as described with respect to FIG. 3. The barrier layer 70 components are described above. Overlying the barrier layer 70 is a semi-permeable outer wall 80, wherein at least one exit orifice 82 is formed. The outer wall 80 is described above. A layer of osmotically-active material 79 also is included in the dosage form 70 in operative contact with the capsule. The layer of osmotically active material 79 surrounds the inner capsule 72 and underlies the outer wall 80. The at least one exit orifice 82 extends therethrough.

FIG. 4C shows an alternative embodiment of a dosage form 90, wherein the inner capsule 92 is coextensive with the barrier layer, i.e., incorporates a laser energy reflecting or transmitting material appropriate for the type of laser to be used. For example, if a carbon dioxide laser is used, the capsule may be composed of a mixture containing a water-soluble polymer, such as gelatin, and any one of the laser energy reflecting or transmitting materials recited above, such as carbon black. The inner capsule 92 is bifunctional, as it defines a reservoir 94 for a therapeutic agent, particularly a liquid therapeutic agent, and functions as a barrier layer to laser ablation either by reflecting or transmitting the laser energy. An osmotically active material layer 99 and an outer semi-permeable wall 96 circumscribe the inner capsule 92. At least one exit orifice 98 is formed through the outer wall and the osmotically active material layer 99 for release of the therapeutic agent during use.

Suitable materials and methods for forming the semi-permeable outer wall of the dosage forms are described, for example, in U.S. Pat. Nos. 4,519,801; 4,612,008, 4,783,337; 4,892,778 and 5,082,668.

It is to be understood that more than one therapeutic agent can be incorporated into the dosage form of this invention. Moreover, the use of the expressions therapeutic agent or drug in no way excludes the use of two or more such therapeutic agents or drugs. The therapeutic agent can be in a wide variety of chemical and physical forms known in the art. For example, the therapeutic agent can be uncharged molecules, components of molecular complexes, nonirritating pharmaceutically acceptable salts, therapeutic derivatives of the therapeutic agent such as ethers, esters, amides, etc., therapeutic derivatives of the therapeutic agent that are easily hydrolyzed by physiological pH, and enzymes, which are all included in this invention.

The amount of a therapeutic agent in the dosage form is an amount sufficient to produce the desired therapeutic response. In practice, this will vary depending upon the particular therapeutic agent, the site of delivery, the severity of the medical condition, and the desired therapeutic effect. Thus, it is often not practical to define a particular therapeutic range for a therapeutically effective dose of the therapeutic active agent incorporated into the dosage form. However, the dosage form will generally contain from about 10 ng to about 1.5 g of the therapeutic agent delivered at the rate from about 0.4 ng to about 65 mg per hour over a 24 hour time period. Suitable therapeutically active drugs are disclosed in, for example, Pharmacotherapy, Vol. 8, pp. 147–157 (1988) and Drugs, Vol. 30, pp. 333–354 (1985).

It will be appreciated that a more general aspect of the invention is the provision of methods for controlling the depth of laser ablation into a dosage form. To form an exit orifice in an outer wall of the dosage form without disturbing an underlying internal compartment containing therapeutic agent, a laser source is pre-selected and operated at parameters which achieve laser ablation of the outer wall while ensuring no ablation of a barrier layer. The barrier layer can contain a material that reflects or transmits the laser energy. For example, powdered stainless steel effectively reflects laser energy from a carbon dioxide layer. Thus, powdered stainless steel could be incorporated into a barrier layer and would provide effective depth control during orifice formation within a selected range of laser operating conditions. Such material would not be suitable for use in a barrier layer when a YAG laser is being used, however, because this type of laser ablates metal materials.

EXAMPLES

Objects and advantages of this invention are further illustrated by the following examples, but the particular materials and amounts thereof recited in these examples, as well as other conditions and details, should not be construed to unduly limit this invention.

Example 1

Preparation of a Liquid Dosage Form Having A Barrier Layer

In experiments performed in support of the invention, commercially available gelatin capsules containing liquid acetaminophen were purchased and spray coated with a solution of 80 weight percent (80 wt %) hydroxypropyl cellulose (Klucel®) and 20 weight percent talc (5% solids in acetone solvent) to a thickness of approximately 0.005–0.020 inch. The coated capsules were dried to remove the acetone solvent. The coated capsules were positioned in the path of a Synrad, model 48-5, 50 Watt sealed-beam carbon dioxide laser operating at 95% power and at various speeds. The laser was focused on the capsules in a pattern that would scribe an orifice having a diameter of approximately 0.020 inch. The laser speeds were 275 mm/sec., 165 mm/sec., 110 mm/sec., and 82.5 mm/sec. The dosage forms were observed for leakage of liquid acetaminophen to determine whether the polymer-talc barrier layer material could reflect the laser energy sufficiently to protect the underlying capsule from being pierced by the laser energy. When the laser was operated at speeds of 275 mm/sec., 165 mm/sec., and 110 mm/sec. the capsule was not pierced and no leakage of liquid therapeutic agent was observed. When the laser was operated at a speed of 82.5 mm/sec., however, sufficient laser energy was absorbed by the underlying capsule to cause piercing and oozing of the acetaminophen liquid from the capsule. Accordingly, it has been discovered that a barrier layer comprising talc can be designed that will prevent laser ablation of an underlying material at selected operating conditions using a carbon dioxide laser.

The complete disclosures of the patents, patent documents, publications, etc., cited herein are incorporated by reference in their entirety as if each were individually incorporated. Various modifications and alterations to this invention will become apparent to those skilled in the art without departing from the scope of the invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A dosage form comprising:
   (a) an outer wall defining an interior compartment;
   (b) a therapeutic agent within the interior compartment;
   (c) at least one laser formed exit orifice in the outer wall; and
   (d) a barrier layer disposed between the outer wall and the interior compartment in at least a region corresponding to the at least one exit orifice, wherein the barrier layer comprises a material that allows the barrier layer to remain intact during formation of the at least one laser formed exit orifice, wherein the material is present in the barrier layer in an amount sufficient to make the barrier layer substantially impervious to laser ablation under a selected laser type and selected laser operating conditions used to form the exit orifice.

2. The dosage form of claim 1, wherein the outer wall comprises a semipermeable material.

3. The dosage form of claim 1, wherein the barrier layer surrounds the interior compartment.

4. The dosage form of claim 1, wherein the barrier layer is a contiguous film.

5. The dosage form of claim 1, wherein the barrier layer is a non-contiguous porous film.

6. The dosage form of claim 1, wherein the interior compartment contains a therapeutic agent in a solid state.

7. A dosage form comprising:
   (a) an outer wall defining an interior compartment;
   (b) a therapeutic agent within the interior compartment, wherein the interior compartment contains a therapeutic agent in a liquid state within a water-soluble capsule;
   (c) at least one laser formed exit orifice in the outer wall; and
   (d) a barrier layer disposed between the outer wall and the interior compartment in at least a region corresponding to the at least one exit orifice, wherein the barrier layer comprises a material that allows the barrier layer to remain intact during formation of the at least one laser formed exit orifice.

8. The dosage form of claim 7, wherein the barrier layer is disposed between the water-soluble capsule and the outer wall.

9. The dosage form of claim 7, wherein the barrier layer is coextensive with the water-soluble capsule.

10. The dosage form of claim 1, wherein the material is capable of reflecting laser energy from the selected laser type under the selected laser operating conditions used to form the at least one laser formed exit orifice.

11. A dosage form comprising:
(a) an outer wall defining an interior compartment;
(b) a therapeutic agent within the interior compartment;
(c) at least one laser formed exit orifice in the outer wall; and
(d) a barrier layer disposed between the outer wall and the interior compartment in at least a region corresponding to the at least one exit orifice, wherein the barrier layer comprises a material that allows the barrier layer to remain intact during formation of the at least one laser formed exit orifice; wherein the material is capable of reflecting laser energy from a selected laser type and under selected laser operating conditions used to form the at least one laser formed exit orifice, wherein the selected laser is a carbon dioxide laser and the material is selected from the group consisting of carbon black, powdered stainless steel, powdered nickel, powdered iron, hydrous magnesium silicate (talc), powdered glass, titanium dioxide, magnesium aluminum silicate, aluminum silicate, aluminum oxide and metallic chips or flakes.

12. The dosage form of claim 1, wherein the material included in the barrier layer is a material capable of transmitting laser energy from a selected laser type and selected laser operating conditions used to form the at least one laser formed exit orifice.

* * * * *